United States Patent [19]

Mimura et al.

[11] 4,349,627

[45] Sep. 14, 1982

[54] PROCESS FOR PRODUCING L-TRYPTOPHAN OR DERIVATIVES THEREOF USING A MICROORGANISM

[75] Inventors: Akio Mimura; Yasuyuki Takahashi; Katsumi Yuasa, all of Fuji; Mitsuru Shibukawa, Yokohama, all of Japan

[73] Assignee: Asahi Kasei Kogyo Kabushiki Kaisha, Osaka, Japan

[21] Appl. No.: 274,566

[22] Filed: Jun. 17, 1981

[30] Foreign Application Priority Data

Jun. 17, 1980 [JP] Japan .................................. 55-80918

[51] Int. Cl.³ .......................... C12P 13/22; C12N 1/20
[52] U.S. Cl. .................................... 435/108; 435/253; 435/822
[58] Field of Search ................................ 435/108, 253

[56] References Cited

FOREIGN PATENT DOCUMENTS 55-45307  3/1980  Japan .................................. 435/108

OTHER PUBLICATIONS

Nakazawa et al., Agricultural and Biological Chemistry, vol. 36, No. 13, pp. 2523-2528, (1972).
Derwent Abstract 85628c/48, (1980) of Japanese 36197/1980.

Primary Examiner—Lionel M. Shapiro
Attorney, Agent, or Firm—Sughrue, Mion, Zinn, Macpeak and Seas

[57] ABSTRACT

A process for producing L-tryptophan or a derivative thereof is disclosed, wherein an indole compound is reacted with serine, or with pyruvic acid and/or its salt and ammonium ion, in the presence of a culture or treated culture of a particular microorganism of genus Enterobacter having a special ability to produce L-tryptophan or a derivative thereof from an indole compound and serine, or from an indole compound, pyruvic acid and/or its salt, and ammonium ion.

4 Claims, No Drawings

PROCESS FOR PRODUCING L-TRYPTOPHAN OR DERIVATIVES THEREOF USING A MICROORGANISM

FIELD OF THE INVENTION

This invention relates to a process for producing L-tryptophan or derivatives thereof by microorganisms, and the microorganisms used therefor.

BACKGROUND OF THE INVENTION

L-Tryptophan is one of the essential amino acids constituting the bodies of animals, and is important as a medicine, nutrient, or as an additive for animal feed. Some L-tryptophan derivatives work as an antagonist against the metabolism of L-tryptophan and contain physiologically active substances that may be used to prepare pharmaceuticals that affect the central nervous system. These L-tryptophan and its derivatives can be produced by known methods of synthesis, biological process and many other methods. Known methods for producing L-tryptophan using microorganisms include: (1) direct fermentation using sugars to accumulate L-tryptophan in a culture; and (2) adding indole or anthranilic acid simultaneously with sugar to a culture, and permitting L-tryptophan to accumulate in the culture. L-Tryptophan can also be produced from indole and serine or from indole, pyruvic acid and ammonium ion by using a microorganism-produced tryptophanase (enzyme). This method of using tryptophanase has the advantage that by varying the type of indole compound, various corresponding L-tryptophan derivatives can be produced, and that hence, a reaction that best suits a particular purpose can be selected.

Many methods are known for producing L-tryptophan using tryptophanase. Japanese Patent Publication No. 46917/74 describes a method wherein L-tryptophan is produced from indole and serine or from indole, pyruvic acid and ammonium ion using a microorganism of genus Escherichia, genus Proteus, genus Pseudomonas, genus Aerobacter or genus Erwinia, and French Pat. No. 1207437, Japanese Patent Application (OPI) No. 39693/72 ("OPI" as used herein means an unexamined published Japanese patent application) and Japanese Patent Publication No. 1836/78 describe a method wherein L-tryptophan is produced from indole and serine using a microorganism of genus Escherichia, genus Claviceps, genus Neurospora, genus Saccharomyces, genus Bacillus, genus Achromobacter or genus Alcaligenes. Several methods are also known for producing L-tryptophan derivatives that correspond to various indole compounds: Japanese Patent Publication No. 46917/74 describes a process for producing 5-hydroxytryptophan using a microorganism of genus Proteus, genus Escherichia, genus Pseudomonas, genus Aerobacter or genus Erwinia; Japanese Patent Publication No. 1835/78 describes a method for producing 5-hydroxytryptophan using a microorganism of genus Achromobacter, genus Escherichia, genus Pseudomonas, genus Alcaligenes or genus Proteus; and Japanese Patent Publication Nos. 5479/76 and 8400/77 describe a method for producing 5-hydroxytryptophan and methoxytryptophan using a microorganism of genus Corynebacterium or genus Brevibacterium.

These methods that use microorganisms are advantageous over the method for producing L-tryptophan or its derivatives by chemical synthesis because they provide only L-form compounds that are optically active. They make possible production of large quantities of L-tryptophan or L-tryptophan derivatives from industrial materials such as indole compounds, serine, or pyruvic acid.

SUMMARY OF THE INVENTION

There has now been found a new microorganism in the soil of the forest in Fuji, Shizuoka, Japan that produces L-tryptophan and derivatives thereof in high yield. Using this microorganism, the invention which is described hereinafter has been accomplished.

This invention provides a process for producing L-tryptophan or a derivative thereof. In the process, an indole compounds is reacted with serine, or with pyruvic acid and/or its salt, and ammonium ion, in the presence of a culture or treated culture of genus Enterobacter SP. AST 49-4 having FERM designation FERM-P 5543.

DETAILED DESCRIPTION OF THE INVENTION

This invention uses genus Enterobacter SP. AST 49-4 having FERM designation FERM-P 5543 that produces L-tryptophan or its derivatives from indole compounds and serine or from indole compounds, pyruvic acid and/or its salt, and ammonium ion.

It is conventionally known that microorganism of tribe Klebsielle that includes genus Enterobacter produce tryptophanase (see *Bergery's Manual of Determinative Bacteriology*, 8th Ed., p. 294). It is also known that various microorganisms produce tryptophanase, which decomposes L-tryptophan to form indole. However, not all microorganisms that produce tryptophanase have the ability to produce a significant amount of L-tryptophan. Microorganisms that produce tryptophanase and which efficiently produce L-tryptophan or its derivatives from indole compounds and serine or from indole compounds, pyruvic acid and/or its salt, and ammonium ion must meet the requirements that the tryptophanase produced in the microorganisms has high activity, that the microorganisms do not decompose the starting materials, such as indole compounds, serine, and pyruvic acid, and that the microoganisms do not decompose the resulting L-tryptophan or its derivatives other than by the tryptophanase.

As a result of extensive studies of a number of tryptophanase-producing microorganisms, the inventors have found a new microorganism of genus Enterobacter that produces L-tryptophan or derivatives thereof in high efficiency. Designated Enterobacter SP. AST 49-4, this microorganism has been deposited with the Fermentation Research Institute, the Agency of Industrial Science and Technology (FERM) under FERM-P 5543 on May 28, 1980.

Mycological properties of Enterobacter SP. AST 49-4 are listed below.

(A) Morphological properties (incubation in nutrient broth at 32° C. for 24 hours)

Shape: short rod, single rods or a chain of two rods, with peritrichous flagella
Size: $1.0$–$1.2\mu \times 1.5$–$3.0\mu$
Motility: present
Gram-staining: negative
Acid fastness staining: negative
Spores: not formed
Pleomorphism: none

(B) Growth in medium (32° C.)

Nutrient broth: good, relatively thick film formed, with precipitate of agglomerated cells, transparent liquid, no pigment formed Nutrient broth agar plate culture: good, irregular contour, rough and wavy surface, raised, undulate periphery, with gloss, slightly Manila paper-colored (i.e., slightly brownish or buff-colored), no pigment formed, slightly viscous Nutrient broth agar slant culture: good, filiform, with gloss, slightly Manila paper-colored, no pigment formed Nutrient broth gelatin stab culture (20° C.): growth good in upper portion, slightly Manila paper-colored, grew in stabbed portion, no gas formed in stabbed portion, not liquefied

(C) Physiological properties

Growth temperature: grew at 13°–42° C., did not grow at 45° C.
Growth pH: 5–9
Oxygen requirement: facultatively anaerobic
OF test (Hugh Leifson's medium): fermented
Gas production (glucose medium): gas produced
Litmus milk: good growth, relatively thick film formed on surface, litmus decolored, milk coagulated
Liquefaction of gelatin: not liquefied
Production of hydrogen sulfide: not produced
Decomposition of starch: not decomposed
Reduction of nitrate: nitrous acid produced
Catalase activity: positive
Oxidase activity: negative
Urease activity: negative
Phenylalanine deaminase activity: negative
Lysine decarboxylase activity: negative
Alginine dihydrolase activity: negative
Ornithine decarboxylase activity: negative
Production of indole: positive
Production of ammonia: positive
VP reaction: positive
MR test: negative
Denitrification: positive
Utilization of citric acid:
    Koser medium: utilized
    Christensen medium: utilized
Sodium chloride fastness: grew in NaCl conc. of up to 2%
Production of pigment (King A medium): not produced
Utilization of nitrogen sources: ammonium salt and nitrate utilized
Utilization of sugars, and production of acid and gas: See Table 1

TABLE 1

|  | Growth | Acid production | Gas production |
| --- | --- | --- | --- |
| D-glucose | + | + | + |
| D-fructose | + | + | + |
| D-mannose | + | + | + |
| D-galactose | + | + | + |
| D-rhamnose | + | + | + |
| D-arabinose | − | − | − |
| L-arabinose | + | + | + |
| D-xylose | + | + | + |
| Sucrose | + | + | + |
| Lactose | + | − | − |
| Maltose | + | + | + |
| Trehalose | + | + | + |
| Raffinose | − | − | − |
| D-inositol | + | + | + |
| D-mannitol | + | + | + |
| D-adonitol | − | − | − |
| D-sorbitol | + | + | + |
| Salicin | + | + | + |
| Glycerin | + | − | − |
| Ethanol | − | − | − |

Isolated from: forest soil at Fuji-shi, Shizuoka, Japan

These are the mycological properties of Enterobacter SP. AST 49-4 according to this invention. Indentification by reference to *Bergey's Manual of Determinative Bacteriology*, 8th Ed., 1974 shows the following: the microorganism belongs to family Enterbacteriaceae because it is a Gram-negative bacillus, has peritrichous flagella, is facultatively ananerobic, is positive in catalase activity, negative in oxidase activity, produces an acid from glucose and reduces nitric acid to nitrous acid, and it belongs most reasonably to genus Enterobacter in tribe Klebsielleae because it is positive in VP reaction, negative in MR test, negative in phenylalanine deaminase activity, grows in a temperature range of from 13° to 42° C., and has motility.

*Enterobacter Aerogenes* ATCC 8724 and *Enterobacter liquefaciens* AJ 2661 are the only two bacteria of genus Enterobacter that are known to produce L-tryptophan from indole, pyruvic acid, and ammonium ion (see *Agricultural and Biological Chemistry*, Vol. 36, p. 2523, 1972). Table 2 compares the properties of Enterobacter SP. AST 49-4 with those of these two bacteria and *Enterobacter cloacae*, another bacterium of genus Enterobacter described in *Bergey's Manual of Determinative Bacteriology*, 8th Ed.

TABLE 2

| Taxonomical properties | Microorganism | | | |
| --- | --- | --- | --- | --- |
|  | AST 49-4 | Enterobacter Cloacae | Enterobacter Aerogenes | Enterobacter Liquefaciens |
| Indole production | + | − | +~−* | − |
| Gelatin liquefaction | − | weak + | weak + | + |
| Lysine decarboxylase activity | − | − | + | + |
| Alginine dihydrolase activity | − | + | − | − |
| Ornithine decarboxylase activity | − | + | + | − |
| Malonate utilization | + | + | + | − |
| Aesculin utilization | + | − | + |  |
| [Acid Production] |  |  |  |  |
| Inositol | + | − | + | + |
| Glycerin | − | − | + | + |
| D-arabinose | − | + | + | + |
| Raffinose | − | + | + | + |
| Adonitole | − | +~−* | + | − |
| Lactose | − | +~−* | + | + |
| [Gas Production] |  |  |  |  |
| Inositol | + | − | + | + |
| Glycerin | − | − | + | + |

*Species include various strains, some being "+", and some "−".

Based on this data on taxonomical properties, we concluded that Enterobacter SP. AST 49-4 is microorganism that differs from any of the bacteria of genus Enterobacter that are described in *Bergey's Manual of Determinative Bacteriology*, 8th Ed. As shown in Table 3 below, Enterobacter SP. AST 49-4 used in this invention achieves a significantly higher yield of L-tryptophan than *Enterobacter aerogenes* ATCC 8724 and *Enterobacter liquefaciens* AJ 2661 described in *Agricultural and Biological Chemistry*, Vol. 36, p. 2523, 1972 under the same reaction conditions, thus demonstrating the industrial value of the microorganism used in this invention.

TABLE 3

| Microorganism | Yield of L-tryptophan* (g/l) |
|---|---|
| *Enterobacter Aerogenes* ATCC 8724 | 11 |
| *Enterobacter Liquefaciens* AJ 2661 | 10 |
| Enterobacter SP. AST 49-4 | 18.6 |

*Amount produced from 20 g/l of indole

This invention relates to a new process for producing tryptophan and derivatives thereof by using Enterobacter SP. AST 49-4 as described above. The microorganism can be cultured on a common synthetic or natural medium. Carbon sources include sugars such as glucose, fructose, mannose, sucrose, galactose, xylose and molasses; sugar alcohols such as glycerin, sorbitol and mannitol; and organic acids such as acetic acid, citric acid, fumaric acid, malic acid and succinic acid. These carbon sources are added to a medium generally in an amount of from about 0.1% to 10% by weight. Nitrogen sources include ammonias such as ammonium chloride, ammonium sulfate, ammonium phosphate, ammonium nitrate, ammonium acetate and ammonia water; and organic nitrogen sources such as urea, meat extract, peptone, Casamino acid, corn steep liquor, defatted soybean meal, and protein hydrolyzate. Substances that promote the growth of the microorganism used are preferably added to the medium. The substances may be inorganic or organic. Inorganic examples include potassium monophosphate, potassium diphosphate, phosphoric acid, potassium chloride, magnesium sulfate and sodium chloride, as well as metal ions such as iron, zinc, manganese, copper and calcium. Organic examples include amino acids, vitamins, organic acids, aliphatic acids, as well as natural substances such as peptone, yeast extract, meat extract, dried yeast, corn steep liquor, casein and defatted soybean hydrolyzate.

Tryptophanase produced by Enterobacter SP. AST 49-4 is considered an adaptive enzyme, and L-tryptophan is preferably added to the medium for preparing a culture of the microorganism in an amount of from about 0.1 to 0.7% by weight. The microorganism is incubated in the resulting medium at from 25° C. to 37° C. for from 16 to 96 hours.

The thus prepared culture of the microorganism has an enzyme system that produces L-tryptophan or its derivatives from an indole compound and serine, or from an indole compound, pyruvic acid and/or its salt, and ammonium ion. The culture may be immediately used in the desired enzymatic reaction, or it may be used after suitable preliminary treatments. For example, the microorganism cells may be separated from the culture by centrifugation or the like. The cells may also be dried, treated with ultrasonic waves, autolyzed or homogenized. Instead, the tryptophanase produced may be extracted and purified by conventional means. Alternatively, the separated cells or enzyme may be used as immobilized cells or enzyme obtained by polymerizing them with an acrylic acid amide monomer or the like.

The thus prepared tryptophanase-containing cells, treated cells and immobilized cells, as well as the purified tryptophanase and the immobilized tryptophanase are used as a catalyst for enzymatic reaction in a reaction liquor comprising an indole compound and serine, or an indole compound, pyruvic acid and/or its salt, and ammonium ion for production of L-tryptophan or its derivatives. In addition to the indole compounds serine, pyruvic acid and/or its salt, and ammonium ion used as substrate, the reaction liquor preferably contains ethylenediaminetetraacetic acid and pyridoxal phosphate for achieving a higher yield of L-tryptophane or derivatives thereof. There is no particular limitation on the amount of the substrate used, and generally it is in the range of from 0.1% to 10% by weight. The enzymatic reaction is usually performed at a pH in the range of from 5 to 11 and at a temperature in the range of from 10° to 60° C. Examples of the indole compound to be added to the reaction system include indole, 5-hydroxyindole, 5-chloroindole, 5-bromoindole, 5-aminoindole, 5-methoxyindole, 5-methoxy-2-methylindole, and 2-methylindole.

The L-tryptophan or its derivatives produced in the reaction liquor can be isolated by conventional methods including adsorption with ion exchange resin, activated carbon, etc. The L-tryptophan and derivatives thereof produced can be verified and quantified by high-pressure liquid chromatography or silica gel thin-layer chromatography.

This invention is now described in greater detail by reference to the following examples, which are given here for illustrative purposes only, and are not intended to limit the scope of the invention.

EXAMPLE 1

Five milliliters of a medium having the formulation indicated in Table 4 was charged into test tubes having a diameter of 18 mm and sterilized at 120° C. for 10 minutes. Each of the sterilized media was inoculated with one loopful of Enterobacter SP. AST 49-4, and cultivated at 32° C. for 20 hours under shaking. Five milliliters of the thus germinated culture was transferred to a fermentation medium prepared by sterilizing 100 ml of a medium (the same as indicated in Table 4) at 120° C. for 10 minutes in a 500-ml shake flask, and fermentation was conducted at 32° C. for 20 hours under shaking. After completion of the fermentation, one liter of the culture was centrifuged to recover the microorganism cells, and the cells were suspended in 200 ml of a reaction liquor (for the formulation, see Table 5), followed by heating at 32° C. for 48 hours under shaking to effect an enzymatic reaction. After completion of the reaction, 10 ml of the suspension was mixed with 10 ml of methanol under vigorous stirring, and the mixture was centrifuged. The resulting supernatant was subjected to high-pressure liquid chromatography; 18.6 g/l of L-tryptophan was found to have been produced in the reaction liquor.

TABLE 4

| Peptone | 2% by weight |
|---|---|
| Casamino acids | 1 |
| Yeast extract | 0.5 |
| Corn steep liquor | 5 |
| L-tryptophan | 0.2 |
| $KH_2PO_4$ | 0.05 |
| $MgSO_4 \cdot 7H_2O$ | 0.05 |

TABLE 4-continued

| | |
|---|---|
| FeSO$_4$.7H$_2$O | 0.003 |
| MnSO$_4$.4H$_2$O | 0.003 |
| pH 7.2 | |

TABLE 5

| | |
|---|---|
| Indole | 20 g |
| Sodium pyruvate | 20 g |
| Ammonium acetate | 20 g |
| Pyridoxal phosphate | 100 mg |
| Ethylenediaminetetraacetic acid | 2 g |
| Water | 1 l |
| pH 9.0 | |

After completion of the reaction, 200 ml of caustic soda was added to the reaction liquor to bring its pH to 10, followed by centrifugation to remove the microorganism cells and provide a supernatant containing L-tryptophan. The supernatant was passed through a column of ammonia type strongly acidic ion exchange resin and the adsorbed L-tryptophan was eluted with 2 N ammonia water. The eluate was concentrated to form a crude L-tryptophan crystal which was washed with acetone and dried to give 2.8 g of an L-tryptophan crystal.

EXAMPLE 2

Enterobacter SP. AST 49-4 was fermented as in Example 1 on a medium having the formulation indicated in Table 4. After completion of the fermentation, one liter of the culture was centrifuged to recover the microorganism cells, and the cells were suspended in 200 ml of a reaction liquor having a pH of 9.0 and consisting of 2 g of indole, 3 g of L-serine, 10 mg of pyridoxal phosphate, 200 mg of ethylenediaminetetraacetic acid and 100 ml of water. The suspension was heated at 32° C. for 36 hours under shaking to effect an enzymatic reaction. After completion of the reaction, 10 ml of the suspension was mixed with 10 ml of methanol under vigorous stirring, and the mixture was centrifuged. The resulting supernatant was subjected to high-pressure liquid chromatography; 21.5 g/l of L-tryptophan was found to have been produced in the reaction liquor.

EXAMPLE 3

Enterobacter SP. AST 49-4 was fermented as in Example 1 on a medium having the formulation indicated in Table 4. After completion of the fermentation, two liters of the culture was centrifuged to recover the microorganism cells and the cells were suspended in 210 ml of a reaction liquor having a pH of 9.0 and consisting of 2 g of sodium pyruvate, 2 g of ammonium acetate, 10 mg of pyridoxal phosphate, 200 mg of ethylenediaminetetraacetic acid and 100 ml of water. The suspension was divided into seven equal amounts and 30 ml of each suspension was mixed with 600 mg of the indole compounds indicated in Table 6, and each mixture was heated at 32° C. for 60 hours under shaking to effect an enzymatic reaction. After completion of the reaction, analysis of the L-tryptophan derivatives produced was conducted by high-pressure liquid chromatography as in Example 1. L-tryptophan derivatives corresponding to the indole compounds used were produced, and the amounts thereof are listed in Table 6.

TABLE 6

| Indole compound | L-tryptophan derivative produced | Amount (g/l) |
|---|---|---|
| 5-Hydroxyindole | 5-Hydroxytryptophan | 3.8 |
| 5-Chloroindole | 5-Chlorotryptophan | 1.9 |
| 5-Bromoindole | 5-Bromotryptophan | 1.7 |
| 5-Aminoindole | 5-Aminotryptophan | 2.1 |
| 5-Methoxyindole | 5-Methoxytryptophan | 1.2 |
| 5-Methoxy-2-methylindole | 5-Methoxy-2-methyl-tryptophan | 1.3 |
| 2-Methylindole | 2-Methyltryptophan | 2.4 |

EXAMPLE 4

Enterobacter SP. AST 49-4 was fermented as in Example 1 on a medium having the formulation indicated in Table 4. After completion of the fermentation, two liters of the culture was centrifuged to recover the microorganism cells, and the cells were suspended in 210 ml of a reaction liquor having a pH of 9.0 and consisting of 1.5 g of L-serine, 10 mg of pyridoxal phosphate, 200 mg of ethylenediaminetetraacetic acid and 100 ml of water.

The suspension was divided into seven equal amounts and 30 ml of each suspension was mixed with 600 mg of the indole compounds indicated in Table 7, and each mixture was heated at 32° C. for 60 hours under shaking to effect an enzymatic reaction. After completion of the reaction, analysis of the L-tryptophan derivatives produced was conducted by high-pressure liquid chromatography as in Example 1. L-tryptophan derivatives corresponding to the indole compounds used were produced, and the amounts thereof are listed in Table 7.

TABLE 7

| Indole compound | L-tryptophan derivative produced | Amount (g/l) |
|---|---|---|
| 5-Hydroxyindole | 5-Hydroxytryptophan | 5.2 |
| 5-Chloroindole | 5-Chlorotryptophan | 2.6 |
| 5-Bromoindole | 5-Bromotryptophan | 2.5 |
| 5-Aminoindole | 5-Aminotryptophan | 2.7 |
| 5-Methoxyindole | 5-Methoxytryptophan | 1.8 |
| 5-Methoxy-2-methylindole | 5-Methoxy-2-methyl-tryptophan | 1.6 |
| 2-Methylindole | 2-Methyltryptophan | 3.4 |

While the invention has been described in detail and with reference to specific embodiments thereof, it will be apparent to one skilled in the art that various changes and modifications can be made therein without departing from the spirit and scope thereof.

What is claimed is:

1. A process for producing L-tryptophan or a derivative thereof, wherein an indole compound is reacted with serine, or with pyruvic acid and/or its salt and ammonium ion, in the presence of a culture or treated culture of the genus Enterobacter microorganism Enterobacter SP. AST 49-4 having the FERM designation FERM-P 5543.

2. A process according to claim 1 wherein the indole compound is selected from the group consisting of indole, 5-hydroxyindole, 5-chloroindole, 5-bromoindole, 5-aminoindole, 5-methoxyindole, 5-methoxy-2-methylindole, and 2-methylindole.

3. A process according to claim 1 or 2, wherein the reaction is carried out at a temperature of 25° C. to 37° C. for from 16 to 96 hours.

4. A biologically pure culture of Enterobacter SP. AST 49-4 having the FERM designation FERM-P 5543, having the ability to produce L-tryptophan or a derivative thereof from an indole compound and serine, or from an indole compound, pyruvic acid and/or its salt, and ammonium ion, by utilizing assimilable sources of carbon, nitrogen, and organic or inorganic substances that promote the growth of the microorganism.

* * * * *